(12) United States Patent
Laniado

(10) Patent No.: US 10,603,204 B2
(45) Date of Patent: Mar. 31, 2020

(54) DEVICE AND METHOD FOR EXTERNAL URINARY INCONTINENCE TREATMENT FOR MEN

(71) Applicant: Tilla Care Ltd., Tirat Carmel (IL)

(72) Inventor: Amir Laniado, Haifa (IL)

(73) Assignee: TILLA CARE LTD., Tirat Carmel (IL)

( * ) Notice: Subject to any disclaimer, the term of this patent is extended or adjusted under 35 U.S.C. 154(b) by 346 days.

(21) Appl. No.: 15/535,414

(22) PCT Filed: Dec. 24, 2014

(86) PCT No.: PCT/IL2014/000066
§ 371 (c)(1),
(2) Date: Jun. 13, 2017

(87) PCT Pub. No.: WO2016/103242
PCT Pub. Date: Jun. 30, 2016

(65) Prior Publication Data
US 2017/0333244 A1 Nov. 23, 2017

(51) Int. Cl.
*A61F 5/443* (2006.01)
*A61F 2/00* (2006.01)
*A61F 5/453* (2006.01)

(52) U.S. Cl.
CPC ............ *A61F 5/443* (2013.01); *A61F 2/0031* (2013.01); *A61F 5/453* (2013.01)

(58) Field of Classification Search
CPC ......... A61F 5/443; A61F 2/0031; A61F 5/453
See application file for complete search history.

(56) References Cited

U.S. PATENT DOCUMENTS

| | | | | |
|---|---|---|---|---|
| 3,194,238 A | * | 7/1965 | Breece, Jr. .............. | A61F 5/455 604/329 |
| 3,721,243 A | * | 3/1973 | Hesterman et al. .. | A61F 5/4404 604/67 |

(Continued)

*Primary Examiner* — Adam Marcetich
(74) *Attorney, Agent, or Firm* — Smith, Gambrell & Russell, LLP.

(57) ABSTRACT

The present invention is a device and method for external urinary incontinence treatment for men that can be self-deployed by a patient or by a care giver. Via the device, a urine removal tube is reversible connected to the glans penis of a treated patient for the removal of urine from a treated patient. The device of the present invention is composed of a penis connecting component and a tube connector component. The tube connector component reversibly contact-connects a urine receiving component to the glans penis of a treated patient. The tube connector component is reversibly connected, anchored and fixated in place to the glans penis of the treated patient by the penis connection component. The connection, disconnection and again reconnection of the penis connection component to the glans penis is easy and simple to carry out.' The connection stabilizes, fixates and adjusts the tightness of the contact-connection between the skin surrounding the orifice of the urethral tract of a treated patient and the urine receiving component. The urine receiving component has spring-like characteristics bestowed by "accordion-like" components that enable a urine leak-free contact-connection while minimizing the discomfort caused to the treated patient.

12 Claims, 7 Drawing Sheets

(56) References Cited

U.S. PATENT DOCUMENTS

| | | | | |
|---|---|---|---|---|
| 3,742,953 | A * | 7/1973 | Lee | A61F 5/453 |
| | | | | 604/352 |
| 4,419,097 | A * | 12/1983 | Rowland | A61F 5/453 |
| | | | | 604/174 |
| 4,681,572 | A * | 7/1987 | Tokarz | A61B 1/307 |
| | | | | 600/574 |
| 4,759,753 | A * | 7/1988 | Schneider | A61F 5/453 |
| | | | | 604/352 |
| 4,784,654 | A * | 11/1988 | Beecher | A61F 5/455 |
| | | | | 604/329 |
| 4,846,816 | A * | 7/1989 | Manfredi | A61F 5/4405 |
| | | | | 604/323 |
| 5,053,027 | A * | 10/1991 | Manfredi | A61F 5/4408 |
| | | | | 600/574 |
| 5,263,947 | A * | 11/1993 | Kay | A61F 5/451 |
| | | | | 600/574 |
| 5,318,551 | A * | 6/1994 | Di Cristo | A61F 5/453 |
| | | | | 128/844 |
| 6,248,096 | B1 * | 6/2001 | Dwork | A61F 5/453 |
| | | | | 604/347 |
| 2005/0101924 | A1 * | 5/2005 | Elson | A61F 5/453 |
| | | | | 604/349 |
| 2009/0048570 | A1 * | 2/2009 | Jensen | B29C 45/0001 |
| | | | | 604/349 |
| 2010/0145314 | A1 * | 6/2010 | Hazan | A61M 25/02 |
| | | | | 604/544 |
| 2011/0230851 | A1 * | 9/2011 | Kay | A61F 5/453 |
| | | | | 604/352 |

* cited by examiner

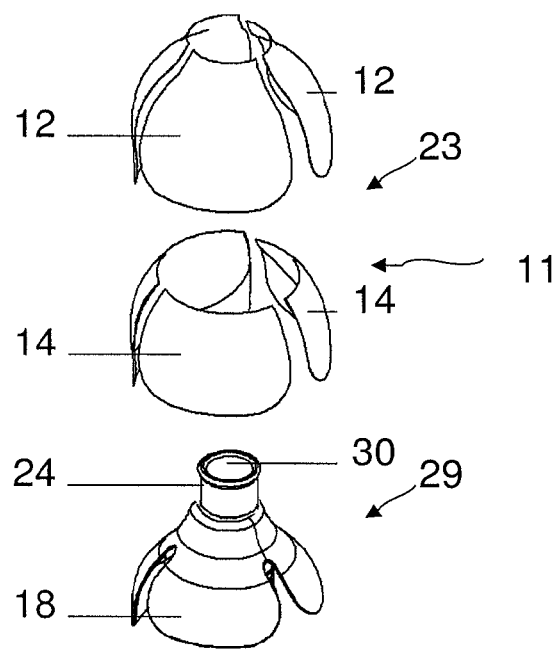
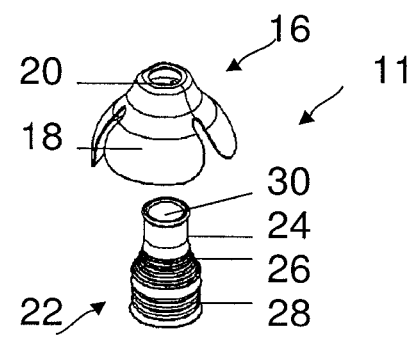
Fig. 3  Fig. 3A
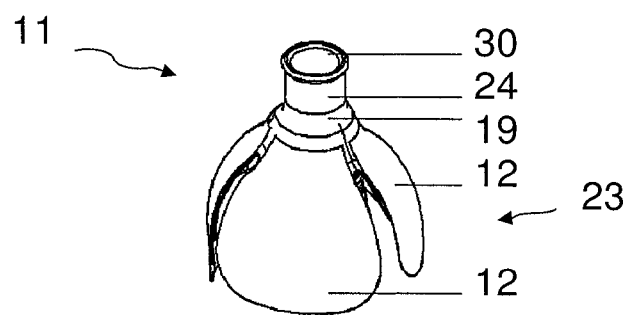
Fig. 4

DEVICE AND METHOD FOR EXTERNAL URINARY INCONTINENCE TREATMENT FOR MEN

FIELD OF THE INVENTION

The present invention relates to a device and method for external urinary incontinence treatment for men. More specifically, the present invention relates to a device and method for the external urinary incontinence treatment for men that reversibly contact-connects a urine receiving component that has spring-like characteristics to the skin surrounding the external urethral orifice in a urine leak-free connection in a that is easy to adjust so as to minimize the discomfort caused to the treated patient. The device of the present invention is self-deployed by a patient or is deployed by a care giver.

BACKGROUND OF THE INVENTION

The preferred treatment of urinary incontinence in men it is often the use of a device that externally connects to the body of the treated patient and collects urine directly from the external orifice of the ureteral tract without penetrating into the orifice. Typically in the various external incontinence treatment devices that have been described in publications, a component that directly receives the urine from the urethral orifice without penetrating the orifice is utilized. The component directs the urine without leaks to a tube that drains the urine to a collection vessel, typically a disposable bag. The urine draining tube is also referred in the following text as: the urine removal tube. The urine receiving component from the orifice of the urethral tract in the text that follows is also referred to interchangeably as the "receiving component" and is also written in an abbreviated form, as: URC.

Some of the disclosed external urinary incontinence treatment devices for men connect the device to the penis by a "condom-like" tube that tightly wraps around the penis and has an opening at the tip that connects to a tube that removes the urine to a collecting vessel, typically a bag. The "condom-like" urinary incontinence treatment devices do not facilitate often and readily adjustment of the devices to the physiology of the treated patients and, when utilized for periods longer than a few hours, the constant tight contact between the large surface area of the devices and the skin of the patients causes skin-irritations. An examples of "condom-like" urinary incontinence treatment devices is give in NL8,602,986 (Wilhelmus).

Another approach for external urinary incontinence treatment devices is reversibly connecting the URC of the device (only) to the glans penis of the treated patient. Such devices substantially reduce the total contact area between the skin of the treated patient and the urinary incontinence treatment device but require, in order to prevent urine leaks, the forming of a stable and tight connection between the skin of the glans penis and the device. Examples of glans penis connected devices are given in: U.S. Pat. No. 5,263,947 (Kay) and PCT/IL2014/000039 (Laniado).

Laniado discloses an external urinary incontinence treatment device that enables the changing of the position and tightness of the connection in the course of treatment between the receiving component and the skin of the glans penis by the use of a locking system. The locking system enables the motion and positioning of the receiving component to provide a desired connection while minimizing the discomfort of the treated patient.

The present invention of a device and method for external urinary incontinence treatment for men provides a device in which the receiving component reversibly connects to the glans penis of the treated patient by an "accordion" pressure mechanism that provides a stable yet substantially better adjustable connection than the connection described in PCT/IL2014/000039.

SUMMARY OF THE INVENTION

The present invention is a device and method for reversibly connecting in an external-body connection, a urine removal tube to the glans penis of a treated patient for the removal of urine to a urine collection vessel (typically a disposable collection bag). The connection, disconnection and again reconnection of the device of the present invention to the glans penis, is easy and simple to establish while minimizing the discomfort created by the connection. The device of the present invention is either self-deployed by a patient or is deployed by a care giver to a treated patient.

The ability of external urinary incontinence treatment devices to collect urine without spills to the surrounding while causing the user minimal discomfort relates to the spatial configuration of the urine receiving component and to the manner in which the receiving component is reversibly connected, adjusted, fastened and fixated to the penis, near and/or over the orifice of the urethra. The term "adjusted" in context of the receiving component of the present invention refers to minor placement and tightening movements of the component to comfortably connect to the skin in the near or over the orifice of the urethra. The term "fastened" in context of the receiving component of the present invention, is used to describe the tightening of the receiving component to the skin surface surrounding the orifice of the urethra of a treated patient in manner that produces a reversible urine leak-free connection. The term "leak-free connection" refers to a connection that prevents the spillage of urine to the surrounding while passing from the urethral tract of the treated patient on its way to a collecting vessel.

The term "contact-connection" in the text refers to a connection in which the connection between surfaces is established and kept by pressuring the surfaces to each other and where no adhesive material nor mechanical means to maintain the connection is used.

The terms "proximal" and "dorsal" in the text relate to a directional reference of either being in the direction towards the body and away from the body of the treated patient, respectively.

The skin of the glans penis is especially sensitive to touch, thus, with an increase of pressure applied to the skin of the glans penis of a treated patient the discomfort caused to the patient increases. In reversibly contact-connecting an URC of an external urinary incontinence treatment device to the skin surrounding the orifice of the urethral tract in the glans penis, it is desired that the contact-connection be leak-free yet be in a tightness that minimizes the discomfort cause to the treated patient.

In accordance to the device and method for the treatment of external urinary incontinence for men of the present invention, devices are constructed of: a urine removal tube connector component (also referred to interchangeably as the: tube connector component and the TCC) and a penis connection component (also referred to as: PCC). The TCC forms a tight urine leak-free contact-connection with the skin that surround the external orifice of the ureteral tract of a treated patient and reversibly connects and communicates freely with a urine-removing-tube that flows the urine discharged from the orifice to a urine collecting vessel, typically a urine collection bag. The PCC reversibly anchors, stabilizes and fixates the TCC to the glans penis of the treated patient.

The TCC is constructed of two connected components: a glans penis stabilization component (also referred to as GPSC) and a urine receiving component (also referred to as: URC). The PCC is constructed of at least one connection-sheet-component (also referred to as: CSC) having a sticky, adhesive material coated layer side, and at least one connection-sheet-protection-component (also referred to as: CSPC) that reversibly connects to the sticky side of the CSC prior to the deployment of the device of the present invention.

Reference is presently made to the construction of the components of a device for external urinary incontinence treatment for men of the present invention.

The components of the TCC, the GPSC and the URC, are produced as a single entity component or, alternatively, they are produced as two separate entity components and are connected prior to the deployment of the device for the treatment of external urinary incontinence for men of the present invention.

The GPSC of the TCC is hollow dome structure made of a semi-rigid flexible material that has a hole at the dorsal, ("top-side") of the dome and least two sheets, referred to as: "stabilizing-sheets", made of a semi-rigid flexible material that protrude and connect to the proximal-side ("bottom side"), circumference rim of the dome. The stabilizing-sheets have a concaved configuration and they fully surround or, alternatively, partially surround, the rim of the hollow dome and form segmented-hollow-dome spatial structure.

The URC is typically produced as a single entity component that is constructed of: a first tube, a hollow dome which extends to hollow tube with a hole at its top, and a second tube. The first tube connects through the tube of the dome and the hollow dome to the second tube. The proximal-side rim of the hollow dome connects to the rim of the second tube. The first and second tube communicate freely between them and enable the free flow of urine from the free opening (proximal side) of the second tube to the free opening (dorsal side) of the first tube. The proximal-side rim of the free opening of the second tube reversibly contact-connects with the skin surrounding the orifice of the urethral tract, the free opening of the first tube connects with a tube that flows urine to a collecting vessel, typically a urine collection bag. The hollow dome and the second tube are interchangeably referred to in the context of the present invention as the: "accordion dome" and "accordion tube", respectively.

The URC connects to the GPSC by inserting the first tube of the URC into the hole (in "top-side") of the dome of the GPSC. The friction between the rim of the hole and the external surface of the tube maintains the connection between the components.

The Internet Dictionary. com (http://dictionary.reference.com/browse/accordion-fold) defines the adjective "accordion" as: having a fold or folds like the bellows of an accordion (musical instrument)". In the context of the present invention the term "accordion tube" and "accordion dome" refers to a tube and dome structures, respectively, constructed of parallel connected hoops. The tubes are constructed of and are connected by a semi-rigid material such as, but not limited to, silicon or rubber. The connected hoops form ribbed-shaped structures that have resiliency in the longitudinal dimension, bestowing flexible spring-like characteristics to the URC. The "accordion configuration" of the dome structure facilitates side-way (swaying) movements of the first tube of the URC and the "accordion configuration" of the accordion tube facilitates, softness yet tightness of the contact-connection between the rim of the proximal opening of the accordion tube and the skin of the glans penis of the treated patient, according to changing patient's body postures and inside URC urine-pressure conditions. The softening of the tightness is achieved by delicately compressing and/or decompressing the accordion tube, thus delicately changing the length of the tube and the pressure applied by the accordion tube to the rim of the tube that is in contact with the skin surrounding the orifice of the ureteral tract.

The CSC of the PCC is composed of a flexible material coated on one side by a sticky, adhesive material coating layer. The CSC is structured as an elongated and flat sheet with a hole at its center. Typically the flat sheet has a "T" configuration. Alternatively, each of two or more connection-sheet-components has a spatial configuration that is part of a segmented-dome structure configuration with a hole at its dorsal ("top") side that is formed when all the sheets are placed one beside the other. The circumference of the rim of the hole fits in its dimension to surround the rim of the hollow-dome of the GPSC.

Each CSPC of the PCC is constructed of a sheet made of a flexible material that reversibly connects to the sticky coating layer side of a CSC and is peeled off from the CSC when the device of the present invention is deployed.

Reference is presently made to the deployment procedure of a device of the present invention:

The GPSC and the URC are connected to form a TCC. The connection is done by inserting the first tube of the URC through the dome of the GPSC. With the components connected, the GPSC is positioned over the glans penis of the treated patient and is pressed in the proximal direction so as to come into contact with the skin. The segmented-dome of the GPSC fits around the glans penis and stabilizes the TCC in its glans-penis contacted position. The proximal side of the URC of the TCC reversibly comes into contact with the skin that surrounds the orifice of the urethral tract of the treated patient. The URC, with its "spring-like" characteristics, softens the urine leak free tight contact-connection between the component and the sensitive skin of the glans penis.

The CSC of the PCC, after the removal of the CSPC, wraps around the GPSC and reversibly connects in an a adjustable connection, by the sticky adhesive material layer, the TCC to the glans penis of the treated patient. The adhesive connection of the CSC to the glans penis anchors, stabilizes and fixates the GPSC in its position. The wrapping around of the GPSC by the CSC and the ability to choose the connection position of the CSC to the glans penis, enables the adjustments of the tightness of the contact-connection of the URC to the skin surrounding the orifice of the ureteral tract of a treated patient. The CSC is/are simply and easily connected, disconnected and again connected to the glans penis of a treated patient in accordance with changes in the posture of the patient and changes in urine discharge (pressure and amount) from the treated patient.

The easy and simple ability to adjust the tightness of the connection by the CSC (by the patient himself or by a care giver) together with the "spring-like" characteristics of the URC, minimizes the discomfort caused to a treated patient when applying the external urinary incontinence device of the present invention to the body of the patient.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

FIG. 3 is an isometric from-above-and-side view of an illustration of a second embodiment of an external urinary incontinence treatment device of the present invention, with the tube connector component and the penis connection component of the device, disassembled.

FIG. 3A is an isometric from-above-and-side view of an illustration of the tube connector component illustrated in FIG. 3 disassembled to a urine receiving component and a glans penis stabilizing component.

FIG. 4 is an isometric from-above-and-side view of an illustration of the external urinary incontinence treatment device illustrated in FIG. 3, with the components of the device assembled.

DETAILED DESCRIPTION OF A PREFERRED EMBODIMENTS

It should be clear that the description of the embodiment and attached Figures set forth in this specification serves only for a better understanding of the invention, without limiting its scope.

Figure 1:
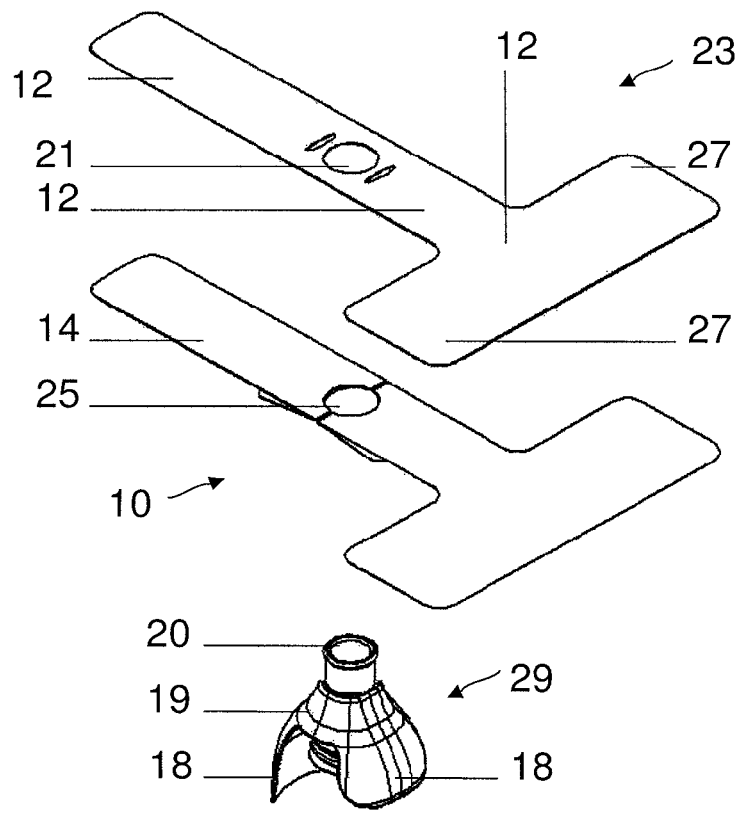
FIG. 1 is an isometric from-above-and-side view of an illustration of an embodiment of an external urinary incontinence treatment device of the present invention, with the tube connector component and the penis connection component of the device, disassembled.
Figure 1A:
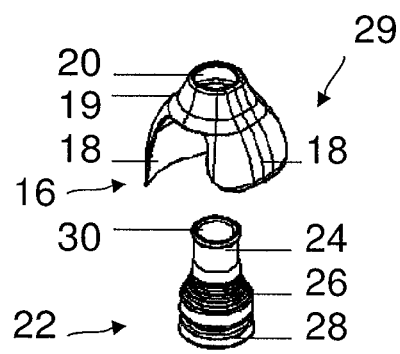
FIG. 1A is an isometric from-above-and-side view of an illustration of the tube connector component illustrated in FIG. 1 disassembled to a urine receiving component and a glans penis stabilizing component.
Figure 2:
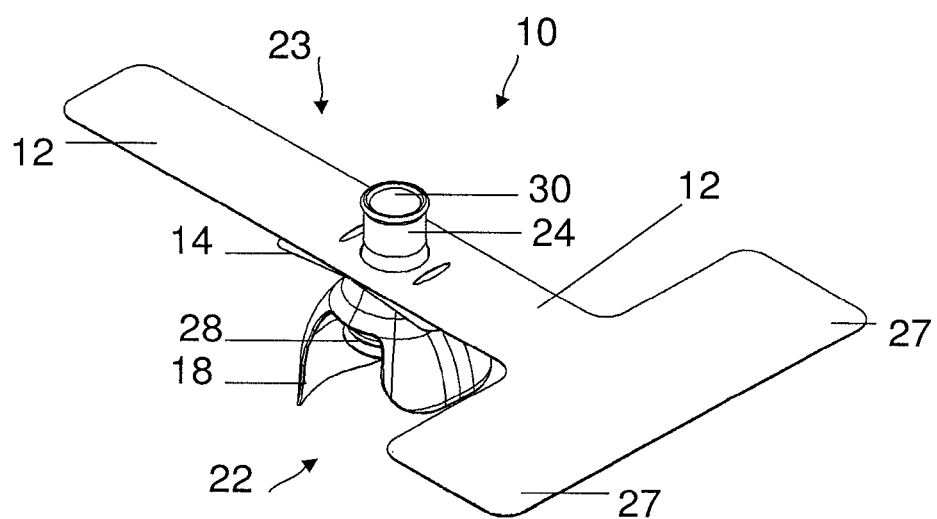
FIG. 2 is an isometric from-above-and-side view of an illustration of the embodiment of the external urinary incontinence treatment device illustrated in FIG. 1 in an assembled configuration.

Two embodiments of the external urinary incontinence treatment device of the present invention are described. The first embodiment is illustrated in FIG. 1, FIG. 1A and FIG. 2, the second embodiment is illustrated in FIG. 3, FIG. 3A and FIG. 4. In the detailed description of the deployment of a device of the present invention, illustrated in FIG. 6A up to and including 6F, the first embodiment of the device of the present invention is shown. The same consecutive stages of deployment illustrated in the figures are relevant for the second embodiment of a device of the present invention.

A device of the present invention (the two embodiments of the device are designated 10 and 11, respectively) is constructed of: a tube connector component (also referred to as TCC) (29) and a penis connection component (also referred to as: PCC) (23).

The TCC (29) is constructed of two connected components: a glans penis stabilization component (also referred to as GPSC) (16) and a urine receiving component (also referred to as: URC) (22). The PCC (23) is constructed of at least one connection-sheet-component (also referred to as: CSC) (12) having a sticky, adhesive material coated layer, side, and at least one connection-sheet-protection-component (also referred to as: CSPC) (14).

GPSC (16) is constructed of a hollow dome structure, referred to as cover-dome (19) with a hole at its dorsal ("top") side (20) and stabilizing-sheet-components (18) that are connected to, and extend radially from, the rim of the dome, at its proximal ("bottom") side. Stabilizing-sheet-components (18) are referred to interchangeably as: SSC Cover-dome (19) is made of a semi rigid material such as, but not limited to, silicone or rubber, or plastic. SSC (18) are structured as at least two sheets also made of semi-rigid flexible material such as, but not limited to, plastic, rubber or silicone. The SSC (18) are connected to cover-dome (19) in a configuration that forms a segmented dome connected to cover-dome (19), shown in FIG. 1A and FIG. 3A. In FIG. 1, two SSCs (18) are illustrated, in FIG. 3, three SSCs are shown. The GPSC (16) is produced as a single-entity component, or, alternatively, cover-dome (19) and the SSC (18) are produced as separate entity components and are connected to form the TCC (29).

URC is constructed of a first tube (24), a dome structure that has a hollow and opened tube that runs through the dome structure and extended from the dome (26) and an accordion tube (28). Tube (24) has an opening hole (30) in its dorsal ("top") side to which a urine-removal-tube tube (31) reversibly connects and through which urine is flowed to a collecting vessel, typically, a urine collection bag (tube (31) shown in FIG. 6F). Tube (24) runs through the tube in dome (26) and connects to the dorsal side of the second tube (28). Tube (24) and tube (28) communicate freely. Dome (26) and tube (28) are structured in an "accordion dome" and "accordion tube" configuration, respectively. The components of the urine-receiving component (22) are made of semi-rigid material, such as, but not limited to, silicon and rubber, or plastic. Urine-receiving component (22) is produced as a single-entity component, or, alternatively, tube (24) dome (26) and tube (28) are produced as separate entity components and are connected to form the urine-receiving component (22).

The CSC (12) of PPC (23) is composed of at least one sheet made of flexible material such as, but not limited to, cloth or plastic or silicone. The sheet has a "sticky" side which is covered by a coating layer of an adhesive material and a plain, "not-sticky" side. The adhesive material can be spread directly on the surface of the sheet, or alternatively, the material is on a thin film that is connected to the surface of the sheet. The adhesive material is present on the surface of the sheet when the sheet is in storage, prior to deployment, or alternatively, the adhesive material is applied just prior to the deployment of the sheet.

In the embodiment (10) illustrated in FIG. 1 and FIG. 2, the CSC (12) is constructed of an elongated single sheet with a hole (21) in the middle. Typically, the elongated sheet has a rectangle configuration with two side protruding portions (27), bestowing a "T" shape configuration to the sheet.

In the embodiment (11) illustrated in FIG. 3 and FIG. 4, the CSCs (12) are constructed of at least two sheet-components with each component having a "slice-of-pie" configuration without the top, "sharp end", section of the slice. The CSCs also have a spatial concave configuration. When placed side by side the CSCs form a hollow sliced dome configuration with a hole at its dorsal top-side.

CSPC (14) is composed of at least one sheet made of a flexible material such as, but not limited to, paper or plastic, or silicon. Each individual CSPC reversibly covers and connects to the sticky side of an individual CSC. The CSPC preserve the stickiness of sticky side on the CSC and are removed from the CSC and discarded prior to the deployment of the device of the present invention.

Reference is Presently Made to the Figures:

FIG. 1 illustrates an isometric from-above-and-side view of an embodiment (10) of an external urinary incontinence treatment device of the present invention, with the TCC (29) and the PCC (23) of the device, disassembled. FIG. 1A illustrates an isometric from-above-and-side view of the TCC (29) illustrated in FIG. 1, disassembled into the URC (22) and the GPSC (16). FIG. 2 illustrates an isometric from-above-and-side view of the embodiment (10) of the external urinary incontinence treatment device illustrated in FIG. 1 in an assembled configuration.

FIG. 3 illustrates an isometric from-above-and-side view of an embodiment (11) of an external urinary incontinence treatment device of the present invention, with the TCC (29) and the PCC (23) of the device, disassembled. FIG. 3A illustrates an isometric from-above-and-side view of the TCC (29) illustrated in FIG. 3 disassembled into the URC (22) and the GPSC (16). FIG. 4 illustrates an isometric from-above-and-side view of the embodiment (11) of the external urinary incontinence treatment device illustrated in FIG. 3 in an assembled configuration.

Figure 5A:
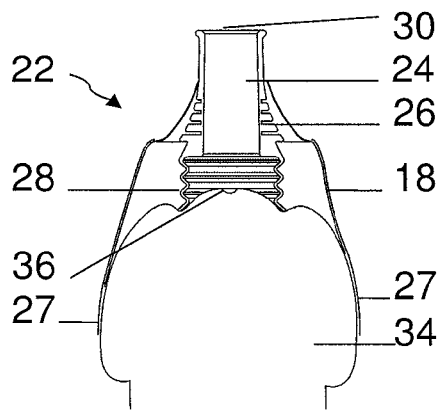
FIG. 5A up to and including 5C are cross cut side-view illustration of consecutive stages of contact-connecting a urine receiving component of the an external urinary incontinence treatment device of the present invention to the skin of the glans penis of a treated patient.

FIG. 5A up to and including 5C are cross cut side-view illustration of consecutive stages of contact-connecting an URC (22) of the of an external urinary incontinence treatment device of the present invention (10, 11) to the skin of the glans penis (34) of a treated patient. The illustrations explain the "spring like" characteristics bestowed by the accordion configuration of the accordion dome (26) and accordion tube (28) to the URC (22).

FIG. 5A illustrates the formation of contact between the URC (22) and the skin surrounding the orifice of the urethral tract (36). Accordion tube (28) is illustrated in a slightly compressed configuration and accordion dome (26) is illustrated in a straight (not bent) configuration.

Figure 5B:
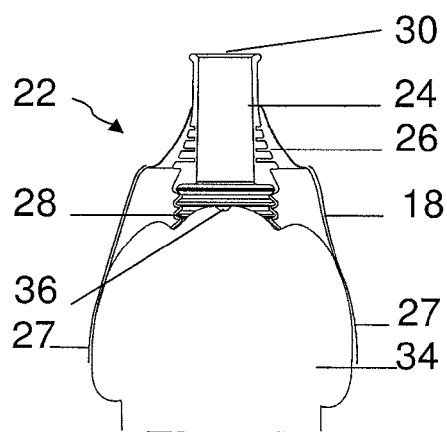

FIG. 5B illustrates the URC (22) in contact with the skin surrounding the orifice of the urethral tract (36). URC (22) is fixated its position with accordion tube (28) illustrated in a compressed configuration and accordion dome (26) illustrated in a straight (not bent) configuration.

Figure 5C:
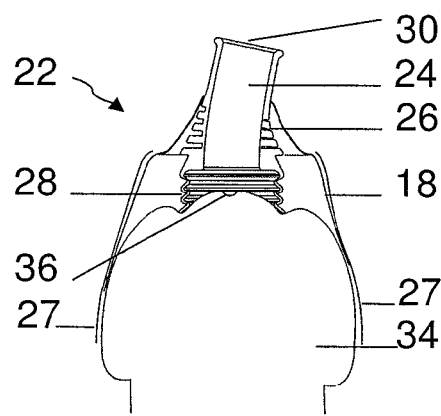

FIG. 5C illustrates the URC (22) in contact with the skin surrounding the orifice of the urethral tract (36) and the tube (24) of the URC (22) connected by a urine-removing-tube (not shown in the figure) that leads to a urine collection vessel. URC (22) is fixated in its position with accordion tube (28) illustrated in a compressed configuration and accordion dome (26) is illustrated in a bent configuration. The bending is caused by the pull and weight of the urine-removing-tube (31) (tube shown in FIG. 6F).

Figure 6A:
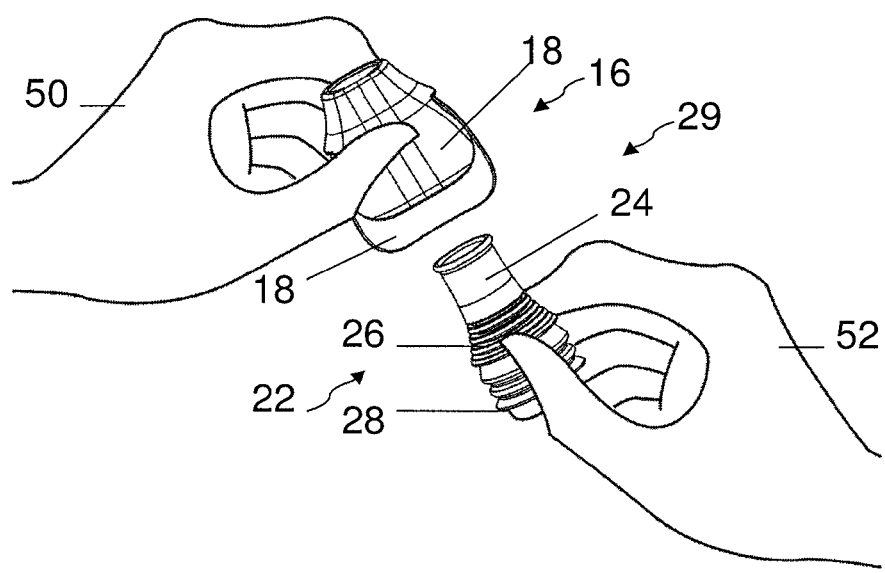
FIG. 6A up to and including
Figure 6B:
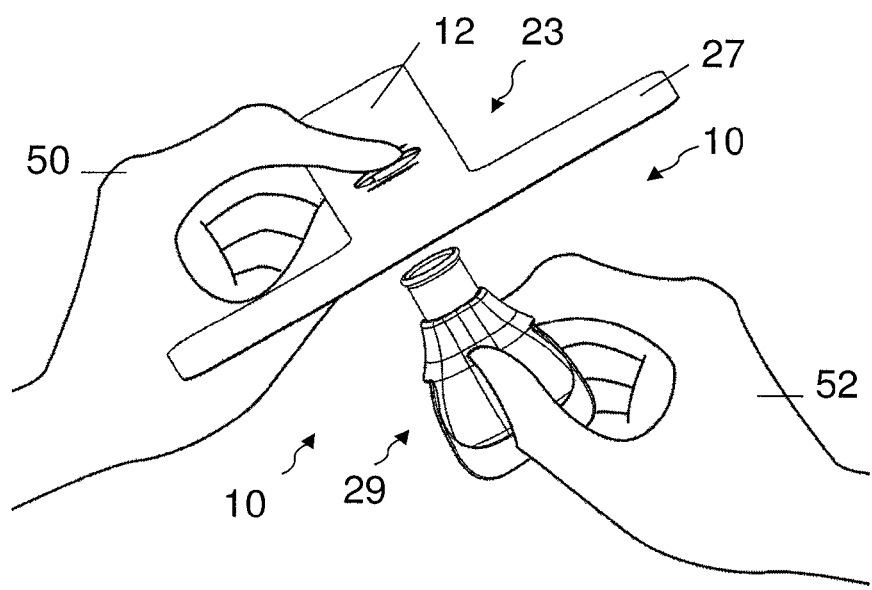
FIG. 6F, are illustrations of consecutive stages of deploying the external urinary incontinence treatment device of the present invention, illustrated in FIG. 1 and FIG. 2.
Figure 6C:
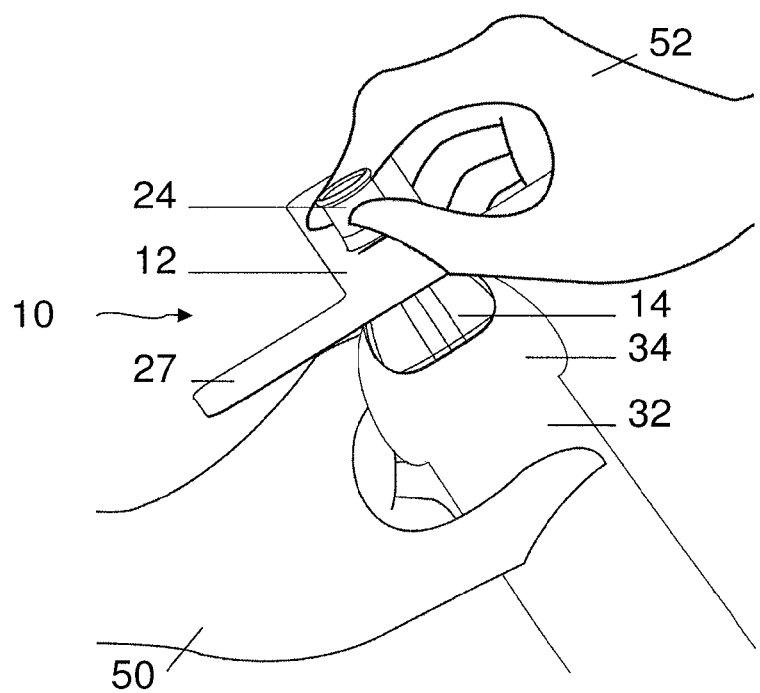
Figure 6D:
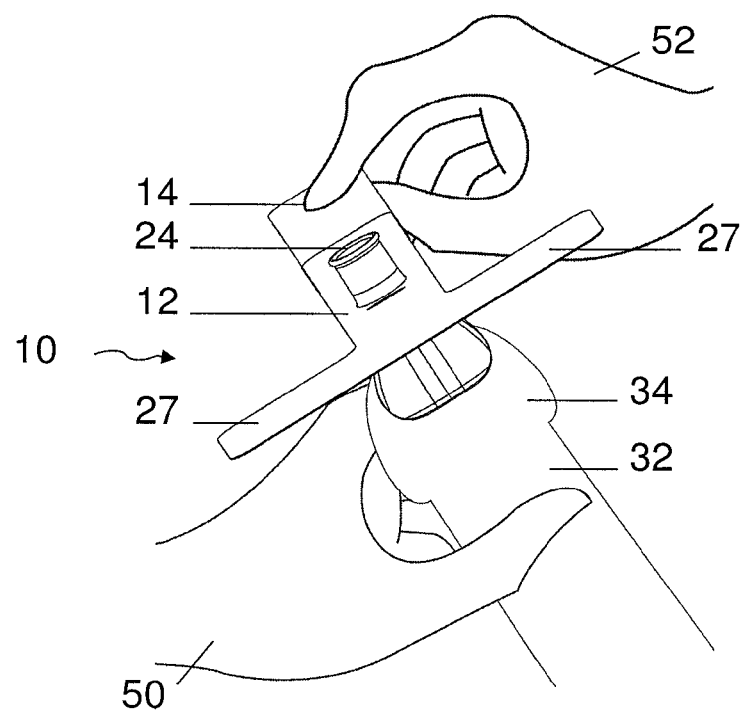
Figure 6E:
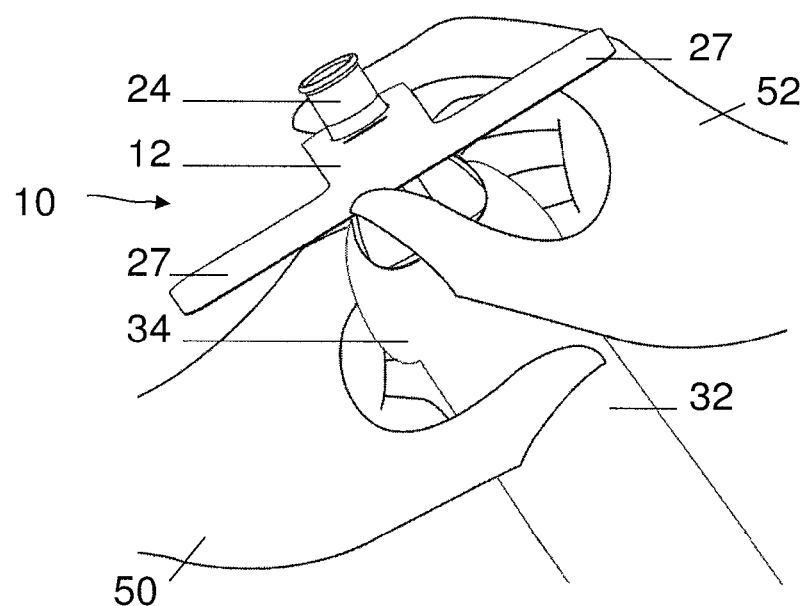
Figure 6F:
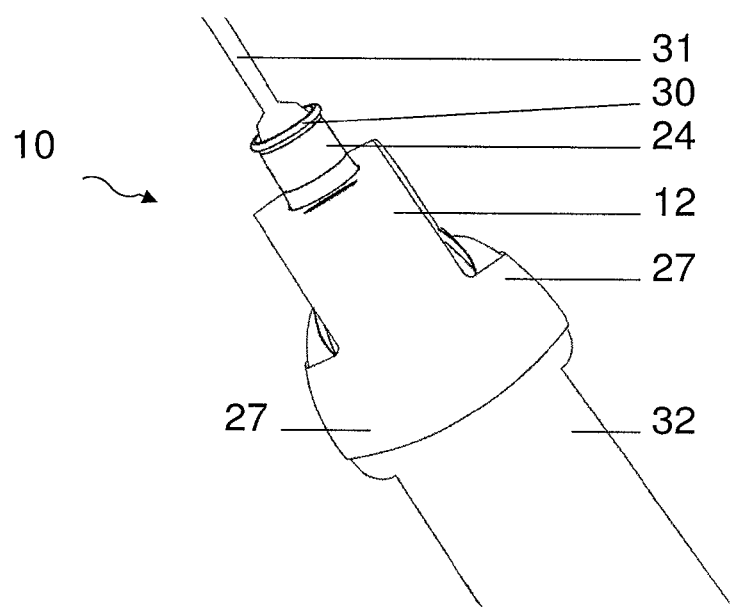

In FIG. 6A up to and including FIG. 6F, the SSC (18) is/are illustrated contact-connected to skin of the glans penis (34), thus stabilizing the TCC (29) in its position over the orifice of the urethral tract and the proximal rim of the accordion tube (28) of URC (22) in contact with the skin surrounding the skin of the orifice of the urethral tract of the treated patient. The CSC (12) of the PCC (23) is/are illustrated warping over (contact-connected) the TCC (29) and reversibly connected (by an adhesive material connection) to the skin of the glans penis (34) of the patient, thus, anchoring, stabilizing and fixating TCC (29) in its position. By disconnecting the connection between CSC (12) and the glans penis (34) and again reconnecting in a different location on the glans penis (34), the tightness as well as the exact positioning of the contact-connection between tube (24) and the skin of the glans penis can be altered and adjusted.

FIG. 6A up to and including FIG. 6F, are illustrations of consecutive stages of deploying the external urinary incontinence treatment device (10).

FIG. 6A illustrates one hand (50) of the patient (or care giver) holding the GPSC (16) while the second hand (52) holding the URC (22). Tube (24) of the URC is placed in an aligned position with hole (20) in the GPSC (16). If the TCC (29) is produced so that the GPSC (16) and the URC (22) are connected to form a single entity component, the deployment of the device is initiated in the following stage, illustrated in FIG. 3B.

FIG. 6B illustrates the insertion of tube (24) of URC (22) Into hole (20) in the GPSC (16), thus, the TCC (29) is connected to the PCC (23) in a "perpendicular configuration".

FIG. 6C illustrates the holding of the penis (32) by the treated patent (or care giver) by one hand (50) and placing with the other hand (52) the rim of accordion tube (28) of the URC (22) on the skin around the orifice of the urethral tract (36) (shown in FIG. 5A).

FIG. 6D illustrates the holding of the penis (32) by the treated patent (or care giver) by one hand (50) and with the other hand (52) the CSPC (14) is peeled off from the CSC (12) by pulling the margin of the CSPC (14) from the CSC (12).

FIG. 6E illustrates the GPSC (16) positioned over the glans penis (34), the URC (22) in contact-connection with the skin surrounding the orifice of the urethral tract of the treated patient (shown in FIG. 5A) and the sticky surface side of the CSC (12) exposed.

FIG. 6F illustrates the final stage of deploying of device (10). The sticky surface of the longitudinal edges of the CSC (12) are folded towards the glans penis (34) and reversibly connect to the circumference skin area beyond the GPSC (16) by the adhesive material. In following, protruding margins (27) of CSC (12) are wrapped around and reversibly connect with the adhesive material to the folded and connected longitudinal edges of the CSC (12) and to the still free skin areas of the glans penis (34). With the TCC (29) fixated in place, urine removing tube (31) is reversibly connected to hole (30) in tube (24).

Figure 7:
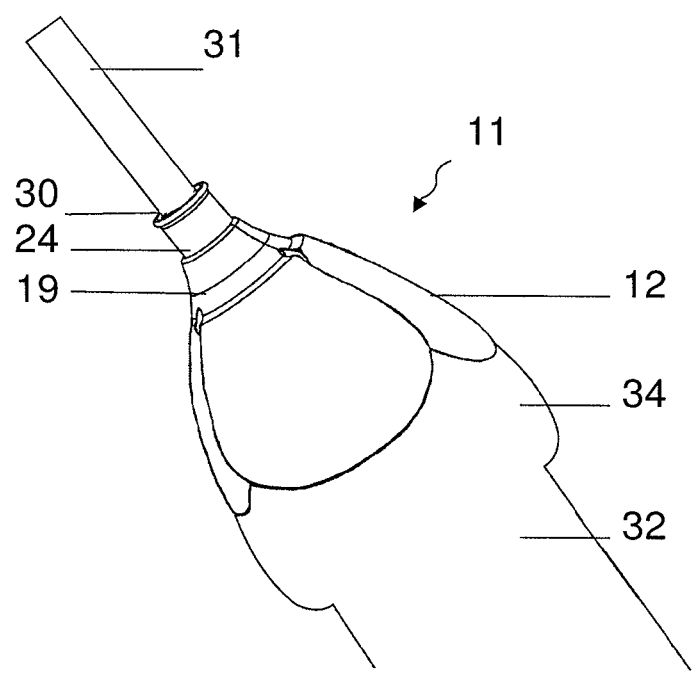
FIG. 7 is an illustration of the external urinary incontinence treatment device of the present invention illustrated in FIG. 3 and FIG. 4 in the final stage of deployment, connected to a urine removal tube.

FIG. 7 is an illustration of the second embodiment of the external urinary incontinence treatment device of the present invention (11) illustrated in FIG. 3 and FIG. 4. The device (11) is illustrated in the final stage of deployment, connected to a urine removal tube (31). In device (11), the TCC (29) is positioned over the glans penis (34), as illustrated in FIG. 6C for embodiment (10). The CSPCs (14) are individually peeled off from the CSC (12) by pulling the CSPCs from the CSCs, as shown for embodiment (10) in FIG. 6D. The exposed sticky sides of the CSCs (12) wrap around the GPSC (16) and reversibly connect to the skin surface of the glans penis (34) that is in the proximal circumference of the glans penis beyond the GPSC (16), as illustrated for embodiment (10) in FIG. 6F. To ensure the stability of the contact-connection of the TCC (29) to glans penis (34), the CSCs (12) overlap.

It should also be clear that a person skilled in the art, after reading the present specification could make adjustments or amendments to the attached Figures and above described embodiments that would still be covered by the present invention.

I claim:

1. An external urinary incontinence treatment device for a male patient that reversibly connects to a urine removing tube comprising:
   a tube connector component including:
      a glans penis stabilizing component constructed of a hollow dome structure with a hole at the top of the dome; and,
      a urine receiving component including a first tube, a hollow dome with a hole at its top, and a second tube, said first tube is inserted through the hole in said hollow dome so as to communicate with said second tube, said hollow dome and said second tube have an accordion configuration,
      wherein said glans penis stabilizing component and said urine receiving component are connected by inserting said first tube of said urine receiving component into the hole in the hollow dome structure of said glans penis stabilizing component, and,
   a penis connection component having at least one connection sheet component having an adhesive material coated layer side, and at least one connection sheet protection component connected to said adhesive material coated layer side of said connection sheet component, said penis connection component includes a hole through which said first tube of said urine receiving component of said tube connector component is inserted.

2. The external urinary incontinence treatment device of claim 1, wherein the glans penis stabilizing component and the urine receiving component of the tube connector component are produced as a single entity component.

3. The external urinary incontinence treatment device of claim 1, wherein the first tube, the hollow dome, and the second tube of the urine receiving component are produced as a single entity component.

4. The external urinary incontinence treatment device of claim 1, wherein the tube connector component is produced of semi-rigid materials.

5. The external urinary incontinence treatment device of claim 1, wherein the penis connection component is produced of sheets made of semi-rigid materials.

6. The external urinary incontinence treatment device of claim 1, wherein the adhesive material coated layer side of said connection sheet component is coated by an adhesive material thin film that is connected to the surface of said connection sheet.

7. The external urinary incontinence treatment device of claim 1, wherein said hollow dome and said second tube are resilient or elastic.

8. The external urinary incontinence treatment device of claim 1, wherein said at least one connection sheet component of said penis connection component has an elongated and flat configuration.

9. The external urinary incontinence treatment device of claim 1, wherein said at least one connection sheet component of said penis connection component forms a segmented-hollow-dome spatial structure.

10. The external urinary incontinence treatment device of claim 1, wherein said glans penis stabilizing component includes at least two stabilizing sheets connected to a circumferential rim thereof.

11. The external urinary incontinence treatment device of claim 10, wherein the stabilizing sheets have a concaved configuration that forms a segmented-hollow-dome spatial structure.

12. A method for the treatment of urinary incontinence treatment of a male by deploying an external urinary incontinence treatment device, the device comprising:
   a tube connector component including:
      a glans penis stabilizing component constructed of a hollow dome structure with a hole at the top of the dome; and,
      a urine receiving component including a first tube, a hollow dome with a hole at its top, and a second tube, said first tube is inserted through the hole in said hollow dome so as to communicate with said second tube, said hollow dome and said second tube have an accordion configuration,
      wherein said glans penis stabilizing component and said urine receiving component are connected by inserting said first tube of said urine receiving component into the hole in the hollow dome structure of said glans penis stabilizing component, and,
   a penis connection component having at least one connection sheet component having an adhesive material coated layer side, and at least one connection sheet protection component connected to said adhesive material coated layer side of said connection sheet component, said penis connection component includes a hole through which said first tube of said urine receiving component of said tube connector component is inserted.

* * * * *